US009361686B2

(12) United States Patent
Dore et al.

(10) Patent No.: US 9,361,686 B2
(45) Date of Patent: Jun. 7, 2016

(54) METHOD AND APPARATUS FOR THE ASSESSMENT OF MEDICAL IMAGES
(71) Applicant: Commonwealth Scientific and Industrial Research Organisation, Australian Capital Territory (AU)
(72) Inventors: Vincent Dore, Heidelberg (AU); Olivier Salvado, Herston (AU); Nicholas Delanie Hirst Dowson, Herston (AU); Jurgen Mejan-Fripp, Herston (AU); Christopher Rowe, Marsfield (AU); Victor Villemagne, Heidelberg (AU); Luping Zhou, New South Wales (AU)
(73) Assignee: COMMONWEALTH SCIENTIFIC AND INDUSTRIAL RESEARCH ORGANISATION (AU)
( * ) Notice: Subject to any disclaimer, the term of this patent is extended or adjusted under 35 U.S.C. 154(b) by 0 days.
(21) Appl. No.: 14/365,745
(22) PCT Filed: Dec. 14, 2012
(86) PCT No.: PCT/AU2012/001536
§ 371 (c)(1),
(2) Date: Jun. 16, 2014
(87) PCT Pub. No.: WO2013/086580
PCT Pub. Date: Jun. 20, 2013
(65) Prior Publication Data
US 2014/0307936 A1 Oct. 16, 2014
(30) Foreign Application Priority Data
Dec. 15, 2011 (AU) ................ 2011905242
(51) Int. Cl.
*G06K 9/00* (2006.01)
*G06T 7/00* (2006.01)
(Continued)
(52) U.S. Cl.
CPC ............ *G06T 7/0016* (2013.01); *G06T 7/0014* (2013.01); *G06T 7/0028* (2013.01);
(Continued)

(58) Field of Classification Search
USPC .................. 382/128, 131, 209, 218, 284, 294
See application file for complete search history.

(56) References Cited

U.S. PATENT DOCUMENTS 6,740,883 B1 * 5/2004 Stodilka ................ G01T 1/1648
250/363.03
7,324,842 B2 * 1/2008 Dale ...................... A61B 5/055
382/128

(Continued)

FOREIGN PATENT DOCUMENTS

WO 2008093057 A1 8/2008

OTHER PUBLICATIONS

Thompson, P., et al. "Mapping Cortical Change in Alzheimer's Disease, Brain Development, and Schizophrenia" Neuroirnage, 2004, vol. 23, pp. S2-S18.

(Continued)

*Primary Examiner* — John Strege
(74) *Attorney, Agent, or Firm* — Tarolli, Sundheim, Covell & Tummino LLP

(57) ABSTRACT

A method of determining the degree of uptake of a PET maker in an individual candidate PET scan, the method including the steps of: (a) calculating a series of representative matched controlled PET and MRI templates for a series of controlled sample scans of individuals; (b) computing a series of brain surfaces from the matched templates; (c) aligning the individual candidate PET scan with the candidate templates; (d) aligning the candidate PET images with the series of brain surfaces; (e) selecting a predetermined (M) best candidate templates for each surface location based on a similarity measure between the candidate PET values and the corresponding controlled PET scans; (f) computing M weights for each surface location, utilizing a corresponding MRI tissue map; (g) utilizing the M weights to combine a corresponding M template tissue indicators from corresponding MRI templates into an average brain surface indicator.

11 Claims, 9 Drawing Sheets

(51) Int. Cl.
  *A61B 5/00* (2006.01)
  *A61B 5/055* (2006.01)
  *A61B 6/03* (2006.01)
  *A61B 8/08* (2006.01)

(52) U.S. Cl.
  CPC .............. *A61B 5/055* (2013.01); *A61B 5/7425* (2013.01); *A61B 6/037* (2013.01); *A61B 8/5207* (2013.01); *G06T 2207/10081* (2013.01); *G06T 2207/10088* (2013.01); *G06T 2207/10104* (2013.01); *G06T 2207/20216* (2013.01); *G06T 2207/20221* (2013.01); *G06T 2207/30016* (2013.01)

(56) References Cited

U.S. PATENT DOCUMENTS

| | | | |
|---|---|---|---|
| 2006/0074290 A1 | 4/2006 | Chen et al. | |
| 2006/0142983 A1* | 6/2006 | Sorensen | A61B 5/055 703/11 |
| 2009/0290765 A1* | 11/2009 | Ishii | A61B 5/055 382/128 |
| 2010/0074480 A1* | 3/2010 | Minoshima | G06T 7/0014 382/128 |
| 2010/0080432 A1* | 4/2010 | Lilja | G06T 7/0012 382/131 |
| 2010/0152577 A1* | 6/2010 | Young | A61B 6/5247 600/431 |
| 2010/0179415 A1* | 7/2010 | Wenzel | G06T 7/0012 600/411 |
| 2010/0215239 A1* | 8/2010 | Assaf | A61B 5/055 382/131 |
| 2011/0129129 A1 | 6/2011 | Avinash et al. | |
| 2011/0172522 A1* | 7/2011 | Shuki | A61B 6/501 600/425 |

OTHER PUBLICATIONS

Collins, D. et al. "Design and Construction of a Realistic Brain Phantom" IEEE Trans. Med. Imag. 17 (3), 1998, pp. 463-438.
Ashburner, J., et al. "Nonlinear Spatial Normalization using Basis Functions" Hum. Brain Mapp. 7 (4), 1999, pp. 254-26).
Ourselin, S., et al, "Reconstructing a 3D Structure from a Serial Histological Sections" Image Vis. Comput 19 (1), 2001, pp. 25-31.
Lopresti, BJ, et al., "Simplified Quantification of Pittsburg Compound B Amyloid Imaging PET Studies: a Comparative Analysis" J. Nucl Med 2005; 46:1959-72.
Joachim, C., et al. "Diffuse Senile Plaques Occur Commonly in the Cerebellum in Alzheimers' Disease" American J. Pathol. 1989, 135 (2), pp. 309-319.
Fripp, J., at al. "Appearance Modeling of 11C PiB PET Images: Characterizing Amyloid Deposition in Alzheimer's Disease, Mild Cognitive Impairment and Healthy Aging" Neuroimage, 2008, 43 (3), pp. 430-439.
Granger, S., et al. "Multi-Scale EM-ICP: A Fast and Robust Approach for Surface Registration" Computer Vision—ECCV, 2002, 2353, pp. 418-432.
Springer et al. "An Efficient EM-ICP Algorithm for Symmetric Consistent Non-Linear Registration of Point Sets" Medical Image Computing and Computer-Assisted Intervention (MICCAI), 2010, pp. 594-601.
Shi et al., "Construction of Multi-Region-Multi-Reference Altases for National Brain MRI Segmentation" NeuroImage, vol. 51, 2010, pp. 684-693.
Svarer et al., "MR-Based Automatic Delineation of Volumes of Interest in Human Brain PET Images Using Probability Maps" NeuroImage, vol. 24, 2005, pp. 969-979.
Aljabar et al., "Multi-Atlas Based Segmentation of Brain Images: Atlas Selection and its Effect on Accuracy" NeueoImage, vol. 46, 2009, pp. 726-738.
Supplemental Partial European Search Report to corresponding European Pat. Appl. No. 12 85 7342, dated Nov. 23, 2015, 4 pages.

* cited by examiner

METHOD AND APPARATUS FOR THE ASSESSMENT OF MEDICAL IMAGES

FIELD OF THE INVENTION

The present invention relates to the field of interpretation and processing of medical images and, in particular, discloses a method and system for the interpretation of marker take up in images such as Positron Emission Tomography (PET) images or Single-photon emission computed tomography images (SPECT) for the detection of anomalies.

BACKGROUND

Any discussion of the background art throughout the specification should in no way be considered as an admission that such art is widely known or forms part of common general knowledge in the field.

The utilization of imaging such as PET or SPECT imaging in the in vitro diagnosing of disease is an important undertaking. This is particularly the case with neurodegenerative diseases such as Alzheimer's disease (AD). The interpretation of suitable imagery is important in gaining an understanding and appreciation of treatment of the disease.

The prior art includes many systems for acquisition and analysis of PET and other image modalities. For example, PCT publication WO2008/093057 to Liljat et al. discloses one such system for the analysis of PET and other imagery in the investigation of AD. Another system is disclosed in US Patent Application Publication No. 2006/074290 to Chen Kewei et al. In all such systems, it is desirable to be able to quickly provide diagnostic information on the state of the imagery.

β-amyloid (Aβ) plaques are among the most prevalent pathological characteristics of Alzheimer's disease (AD), which can appear many years before the dementia is diagnosed. The recent development of functional imaging agents makes it possible to assess amyloid deposition in vivo. One promising known radiotracer is Pittsburgh Compound-B ($^{11}$C-PiB), which binds with high affinity and high specificity to Aβ plaques. It has been shown that AD patients tend to have higher PiB binding in cortical regions than normal controls. Other important Amyloid imaging compounds are being developed such as Florbetapir, and could also be utilized with the present invention.

The assessment of PiB uptake with different tissue types (grey matter, white matter, and CSF) in cortical regions can facilitate the diagnosis and monitoring of the dementia. However, due to the low resolution and the lack of structural information in PET images, the existing approaches usually rely on concurrent MRI images for the determination of tissue regions. Further, the binding pattern of the marker is often unrelated to the underlying tissue structure and can be highly variable. The common process such as those disclosed in Lilja et al. involves a concurrent tissue segmentation on an MRI image and a multi-modular registration between MRI and PET images for each subject.

Although such estimations are relatively accurate, MRI-independent assessment methods are desirable due to clinical settings and the absence of MRI scans due to various reasons (e.g. claustrophobia, metallic implants, etc. . . . ).

SUMMARY OF THE INVENTION

It is an object of the present invention to provide for an improved form of assessment of the uptake of a marker in medical images such as PET or SPECT images.

In accordance with a first aspect of the present invention, there is provided a method of determining the degree of uptake of a PET maker in an individual candidate PET scan, the method including the steps of: (a) calculating a series of representative matched controlled PET and MRI templates for a series of controlled sample scans of individuals; (b) computing a series of brain surfaces from the matched templates; (c) aligning the individual candidate PET scan with the templates; (d) aligning the series of brain surfaces with the candidate PET image; (e) selecting a predetermined (M) best candidate templates for each surface location based on a similarity measure between the candidate PET values and the corresponding PET templates; (f) computing M weights for each surface location, utilizing the corresponding MRI templates tissue maps and similarity measures between the candidate PET and the PET templates; (g) utilizing the M weights to combine the corresponding M template tissue indicators to estimate the candidate PET uptake at each location of the average brain surface indicator.

The method preferably also includes the step of: (h) combining the average brain surface with the candidate PET scan data to create a combined averaged brain surface for display. In some embodiments, the step (c) can comprise utilizing candidate CT or X-Ray scan data in the alignment of the candidate PET images with the series of candidate templates.

In accordance with a further aspect of the present invention, there is provided a method of determining the degree of uptake of an imaging maker in an individual candidate imaging marker scan, the method including the steps of: (a) calculating a series of representative matched controlled imaging marker scans and tissue marker templates for a series of controlled sample scans of individuals; (b) computing a series of internal body delineation surfaces from the matched templates; (c) aligning the individual candidate imaging marker scan with the candidate templates; (d) aligning the individual candidate imaging marker scan with the series of body delineation surfaces; (e) selecting a predetermined (M) best candidate templates for each surface location based on a similarity measure between the candidate imaging marker values and the corresponding controlled imaging marker scans; (f) computing M weights for each surface location, utilizing a corresponding tissue marker map and similarity measures; (g) utilizing the M weights to combine a corresponding M template tissue indicators from corresponding tissue templates into an average brain surface indicator.

The imaging marker scans can comprise Positron Emission Tomography (PET) scans or Single-photon emission computed tomography (SPECT). Each tissue marker template can be calculated from images of different subjects with known image properties. The multiple tissue templates are preferably selected from a wider set of templates in accordance with similar characteristics of the candidate and subjects with known image properties. The templates and candidate images are preferably segmented.

In accordance with a further aspect of the present invention, there is provided a method of determining the brain uptake of an imaging marker in a subject image, the method including the steps of: preparing a series of brain templates from controlled sample images, the templates including co-registering a series of controlled sample images, and creating a probability map containing an approximation of the likelihood that a particular atlas voxel contains grey matter; determining from the brain templates, a correspondence surface between grey and white matter interfaces; for the given subject image, mapping the subject image to a corresponding brain template; and mapping the correspondence in grey matter uptake for the subject image for grey area portions of the brain templates. The controlled sample images can include both PET and MR images.

The correspondence can be measured in a predetermined direction relative to the surface between grey and white matter. The mapping can occur for multiple templates. The multiple mappings are preferably combined utilizing a Bayesian network or a weighted sum or voting rules or other fusion techniques.

BRIEF DESCRIPTION OF THE DRAWINGS

Preferred embodiments of the invention will now be described, by way of example only, with reference to the accompanying drawings in which:

FIG. 6 illustrates a comparison of the multi-atlas approach and the single-atlas approaches based on averaged errors per vertex between the PET and the MRI-dependent methods. The multi-atlas approach consistently generates lower errors for almost all the 104 test subjects.

FIG. 7 illustrates a comparison of the proposed multi-atlas approach and the single-atlas approaches based on averaged ROI vertex errors between the PET and the MRI-dependent methods. The multi-atlas approach consistently generates lower errors for all the ROIs.

DETAILED DESCRIPTION

Figure 1:
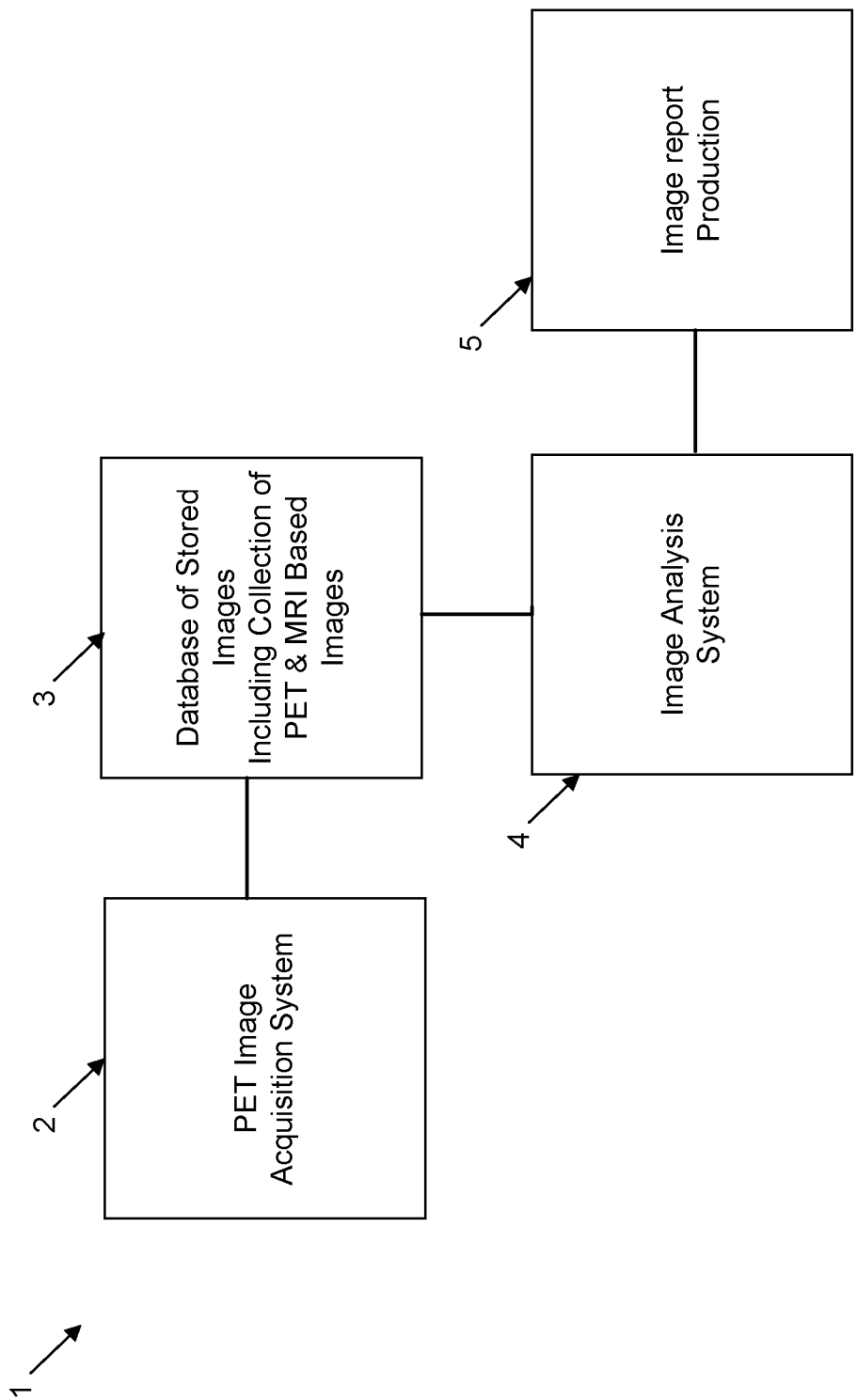
FIG. 1 illustrates schematically one form of operational environment for execution of the preferred embodiment.

In the embodiments of the present invention, there is provided a "PET-image-only" method, which registers a region of interest (ROI) atlas to a subject's PET images and averages the PiB uptake values within the ROIs. Where only a single atlas is involved, the estimation accuracy of this method can be dependent on the selection of the atlas and the registration errors. It has been found through the utilization of multiple atlases, improved results are obtained. The embodiments provide a more robust "PET-only" method that improves the posterior probability of the assessment. To achieve this, three major strategies are employed as follows:

1. A tissue probability map is introduced to guide the measurement of the PiB values, instead of the hard ROI partitions copied from a single warped ROI atlas. The probability map is the prior knowledge learned from a training set, therefore incorporating the population variations, and becoming more robust than the ROIs simply obtained from a single atlas image.

2. Multiple atlases are used to cancel out the registration errors from a single atlas. The utilization of multiple atlases also allows for each PET image to be from a different PET atlas. The use of multiple PET atlases allows for the selection of each location of subject matter in the database to be similar. In other words, the method of the second example embodiment can use for a given patient, the templates A, B, C for a pixel in the frontal lobe, and templates C, D, E for a pixel on the temporal lobe.

A subject-specific optimal subset of atlases can be selected from a large pool of atlases, and combined by a Bayesian framework to improve the posterior probability of the estimation. The weights to combine the different templates can be varied pixel by pixel. The PiB uptake values are then directly estimated, which avoids the explicit need for segmentation of grey matter. Therefore using multiple atlases statistically reduces the registration and sampling error found in each individual atlas.

3. In addition to the population-based probability maps that are obtained from the atlases, subject-specific probability maps are also utilized by using nonlocal means segmentation of the subject PET image. This also provides a methodology for computing the weights at each pixel. With multiple atlases, such a segmentation derives the probability map specifically for the particular subject based on population information, and thus improves the estimation of the priors and the posteriors further.

Compared with the prior art approaches, that normally require both MRI and PET images for a precise estimation of PiB uptake within grey matter, the embodiments are able to utilise only PET images, yet still provides a reasonably accurate estimation that has small estimation errors, and high correlations with MRI-based methods. Although the proposed method has general application for both volume-based and surface-based PiB assessments, a surface based measurement is initially described. A volume-based measurement is relatively simpler and can be conducted similarly without using the surface model.

The method provided by the embodiments can be used as a clinic inspection tool for the diagnosis and monitoring of the Alzheimer's disease. However, the method can be applied to other PET markers of Amyloid (AV1), and is general enough to be applied to any other PET markers for any pathology, and to any other SPECT markers for any pathology.

Turning initially to FIG. 1, there is illustrated the operational environment 1 for implementation of the preferred embodiments. In this environment, PET images are scanned 2 for storage in a database 3 for processing. Image analysis system 4 carries out the image analysis method of the preferred embodiments and outputs an image report 5 including a number of measures.

Figure 2:
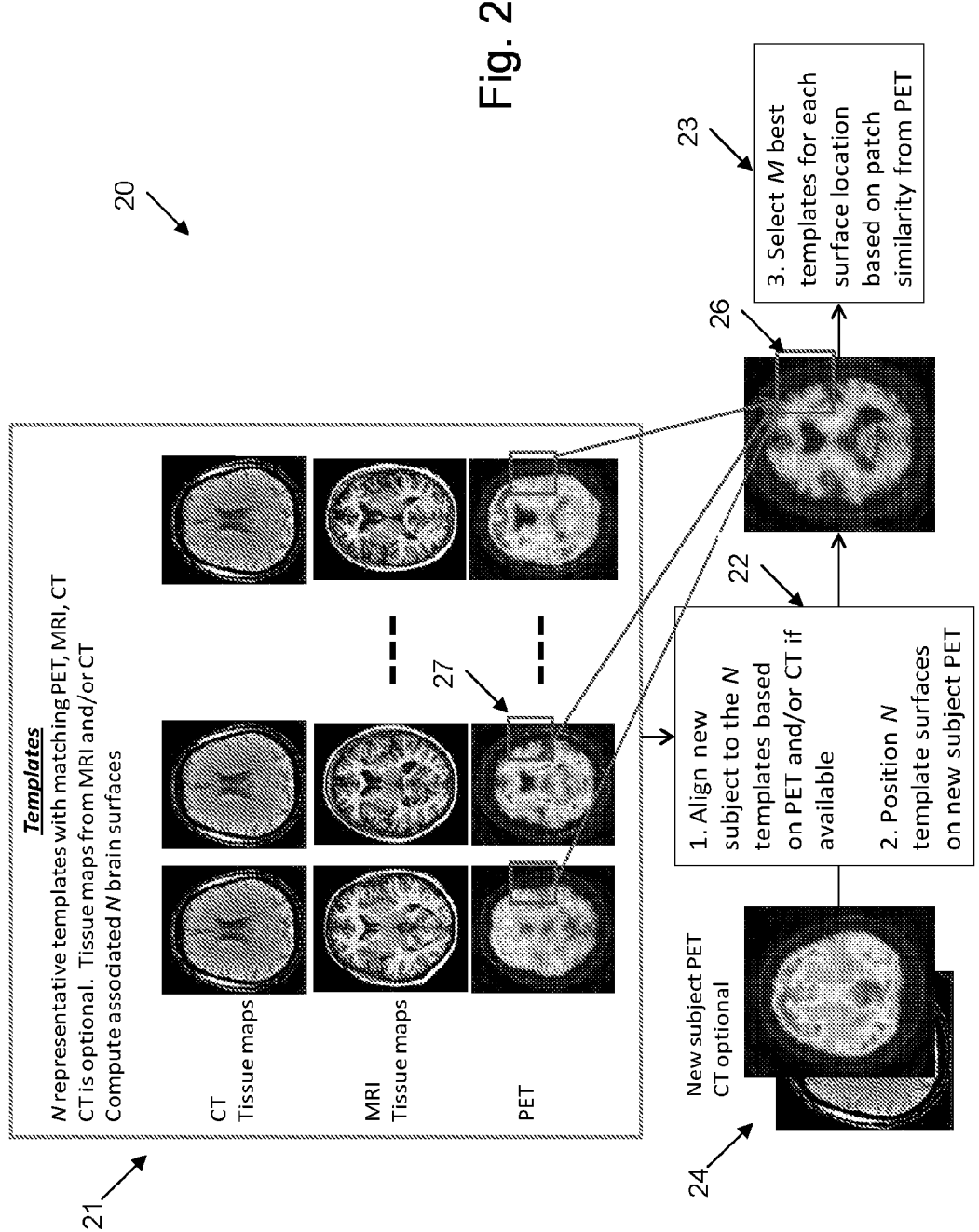
FIG. 2 illustrates a first portion of a flow chart of the steps of the preferred embodiments.
Figure 3:
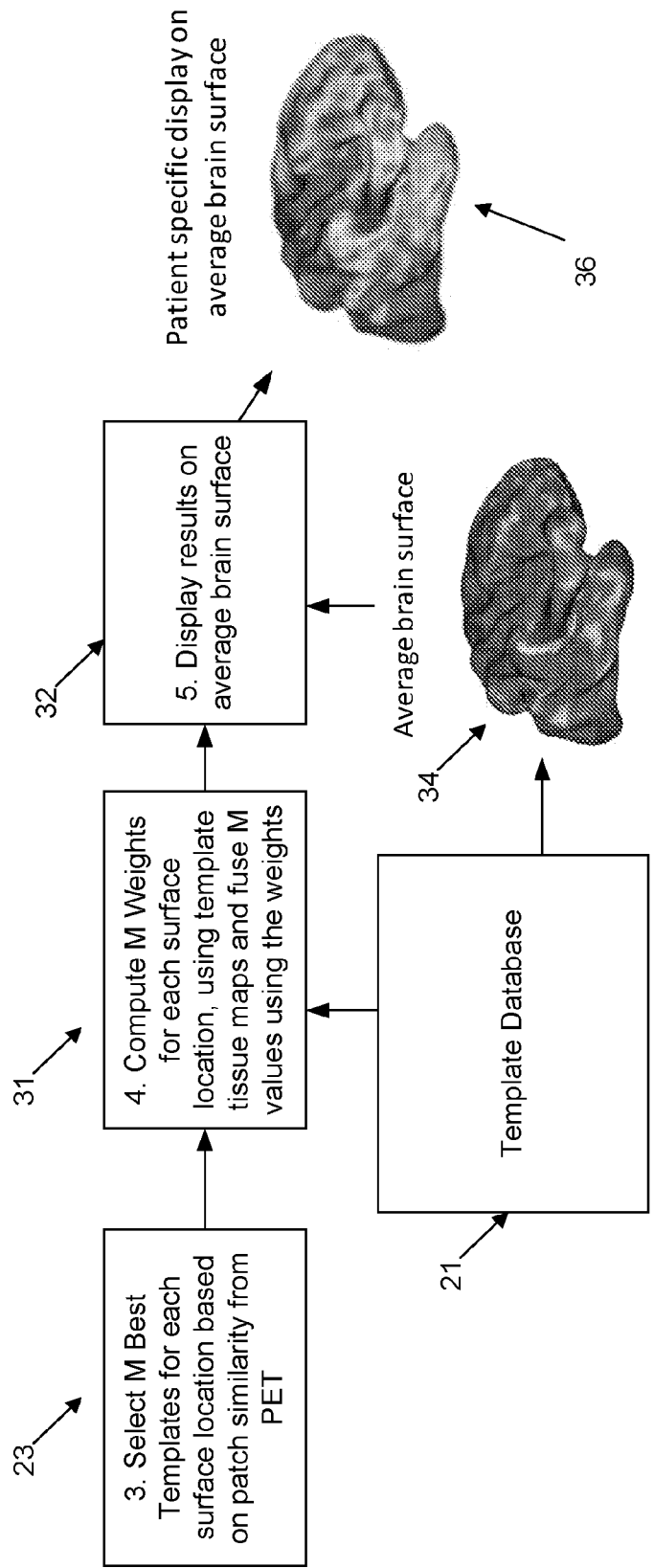
FIG. 3 illustrates a second portion of a flow chart of the steps involved in the preferred embodiment.
Figure 4:
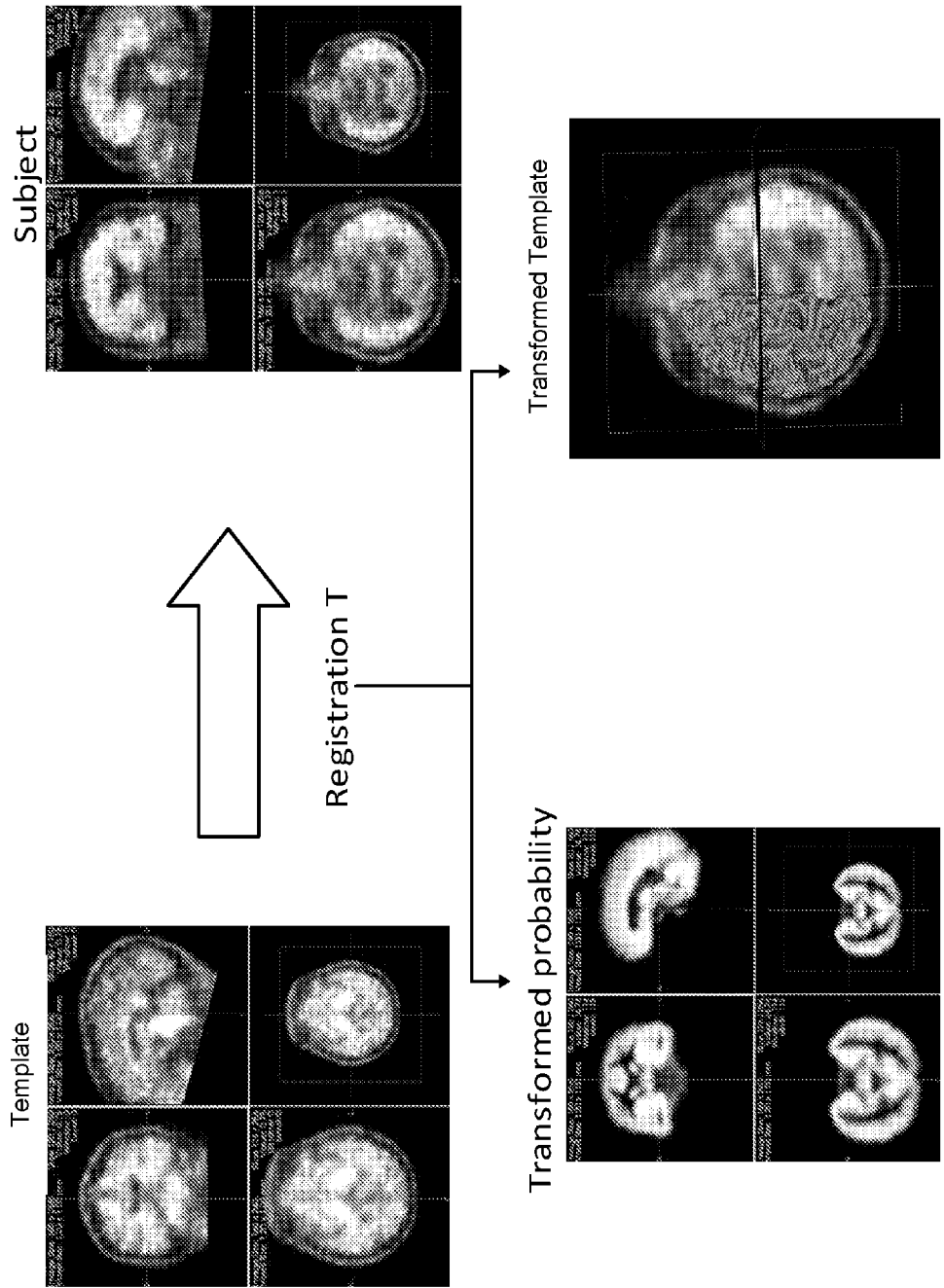
FIG. 4 illustrates the process of template registration.
Figure 5:
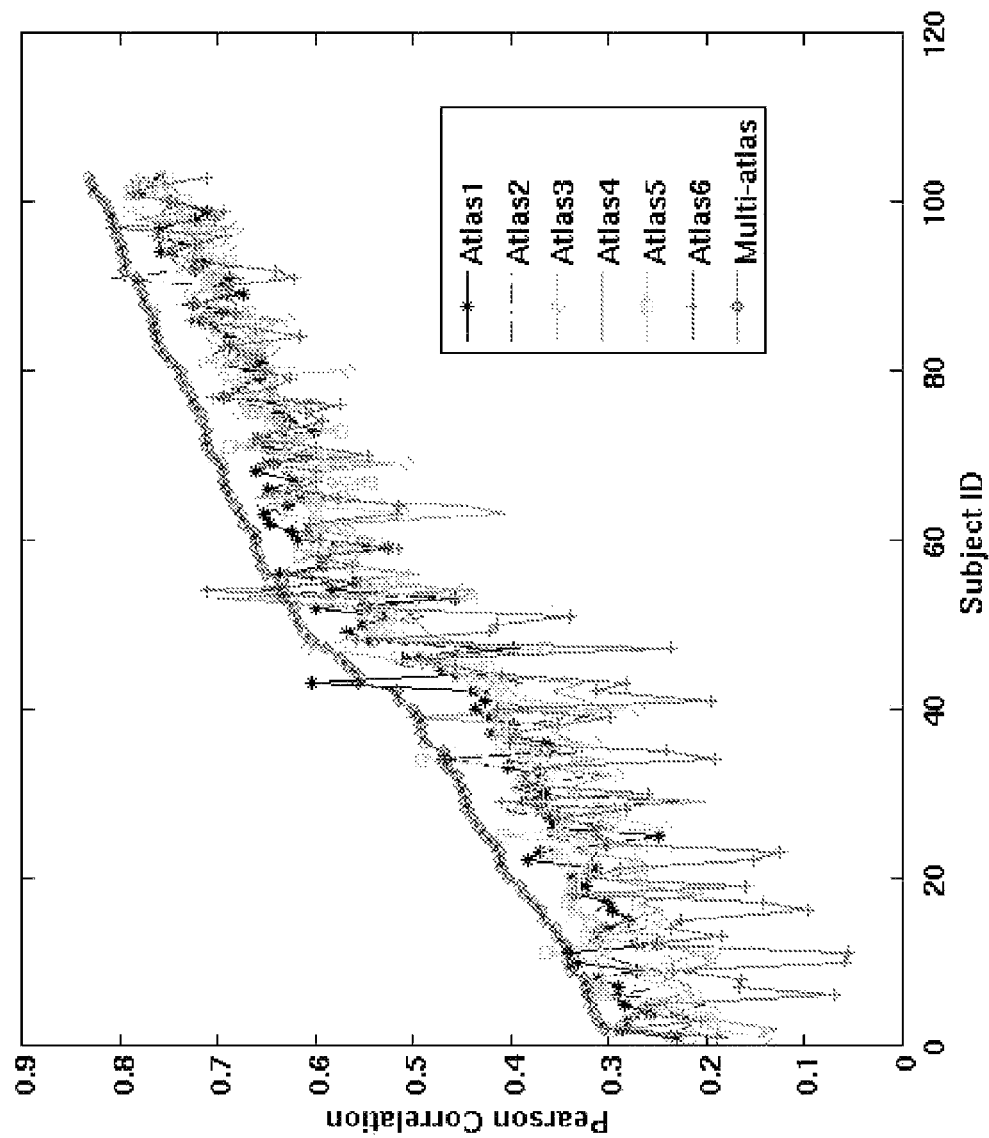
FIG. 5 to FIG. 8 are graphs of mapping results of mapping subjects to template or atlas values; with FIG. 5 showing a comparison of a multi-atlas approach and the single-atlas approaches based on averaged correlation coefficients with the MRI-dependent method. The multi-atlas approach was shown to consistently generate higher correlations for almost all the 104 test subjects.
Figure 6:
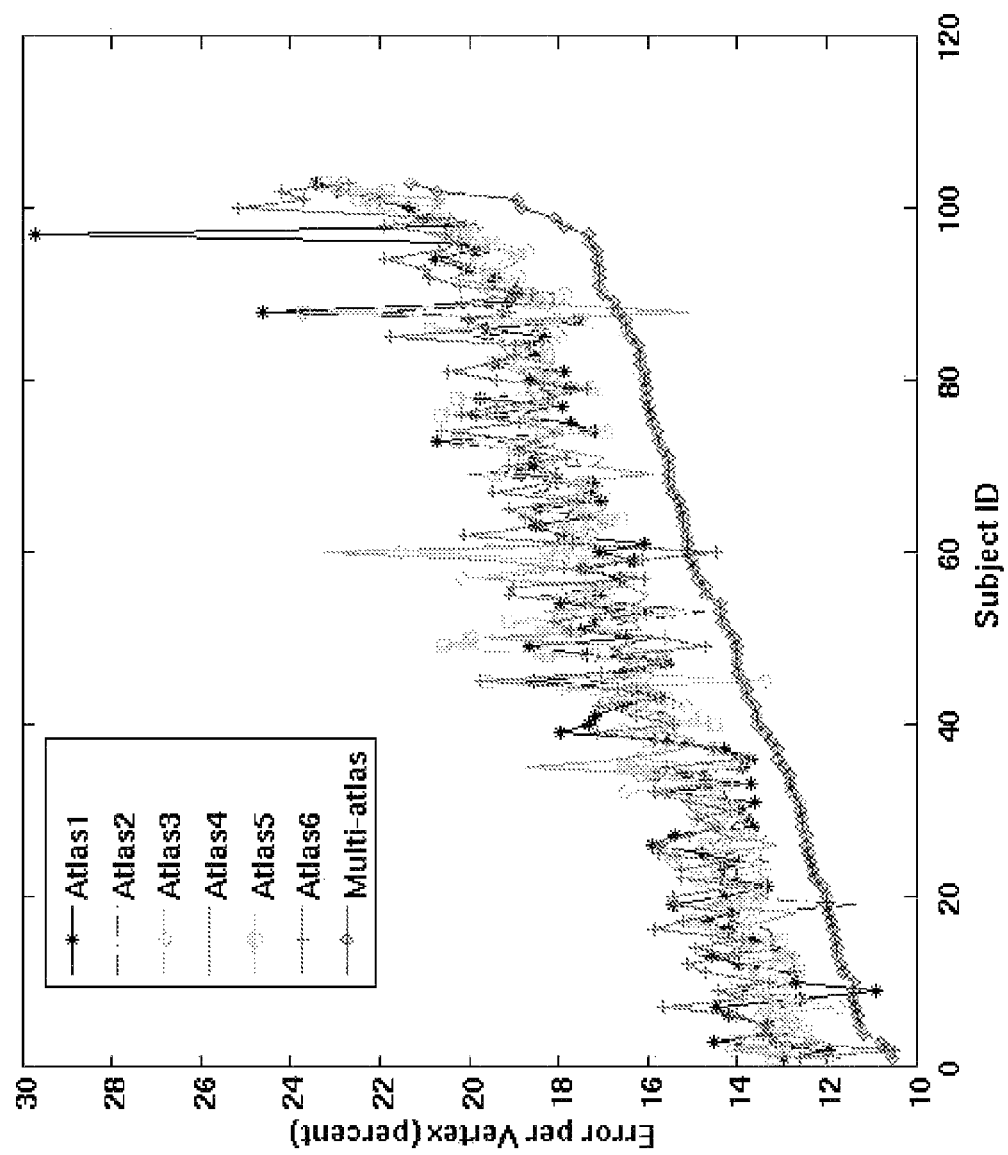
Figure 7:
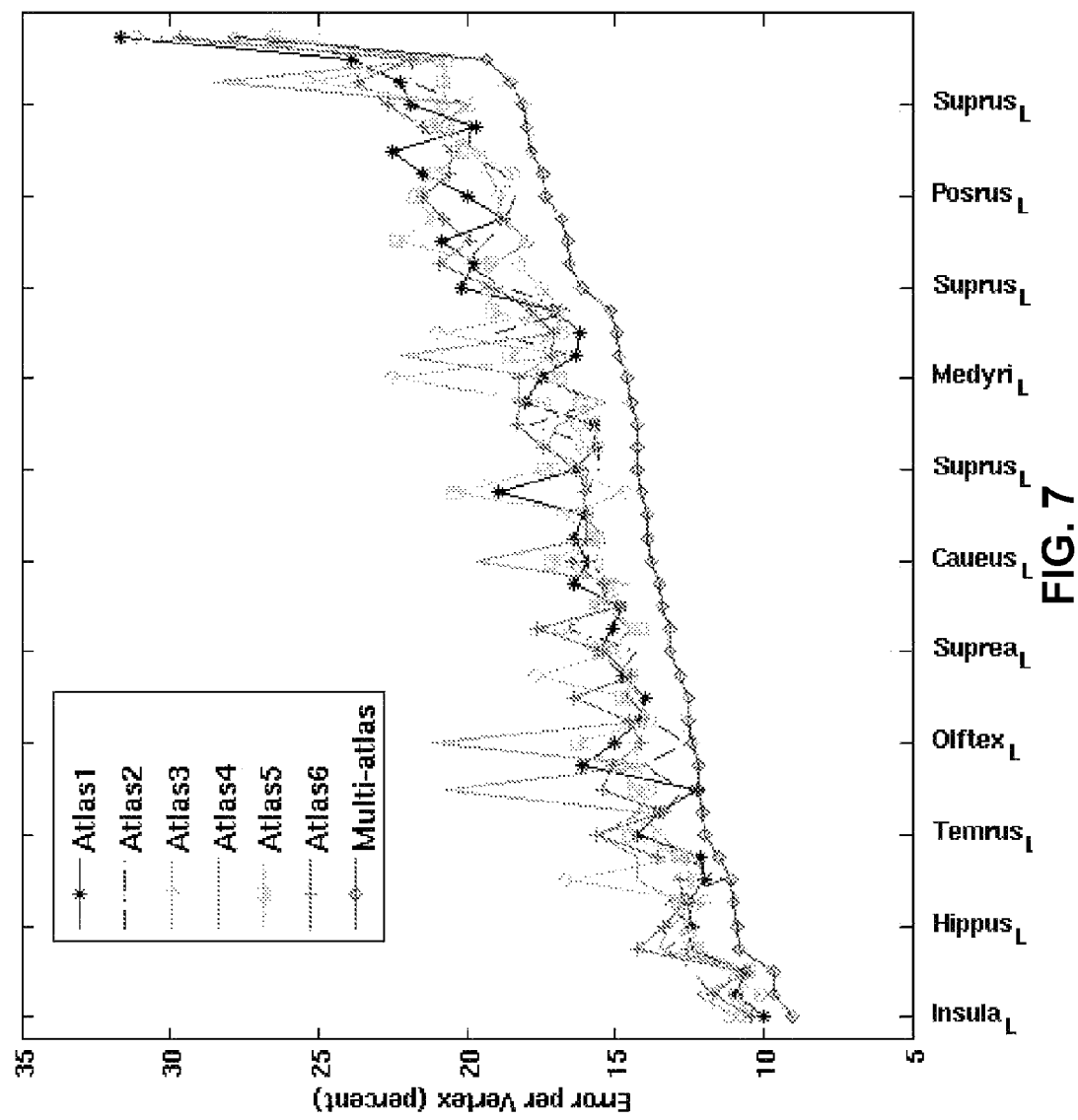
Figure 8:
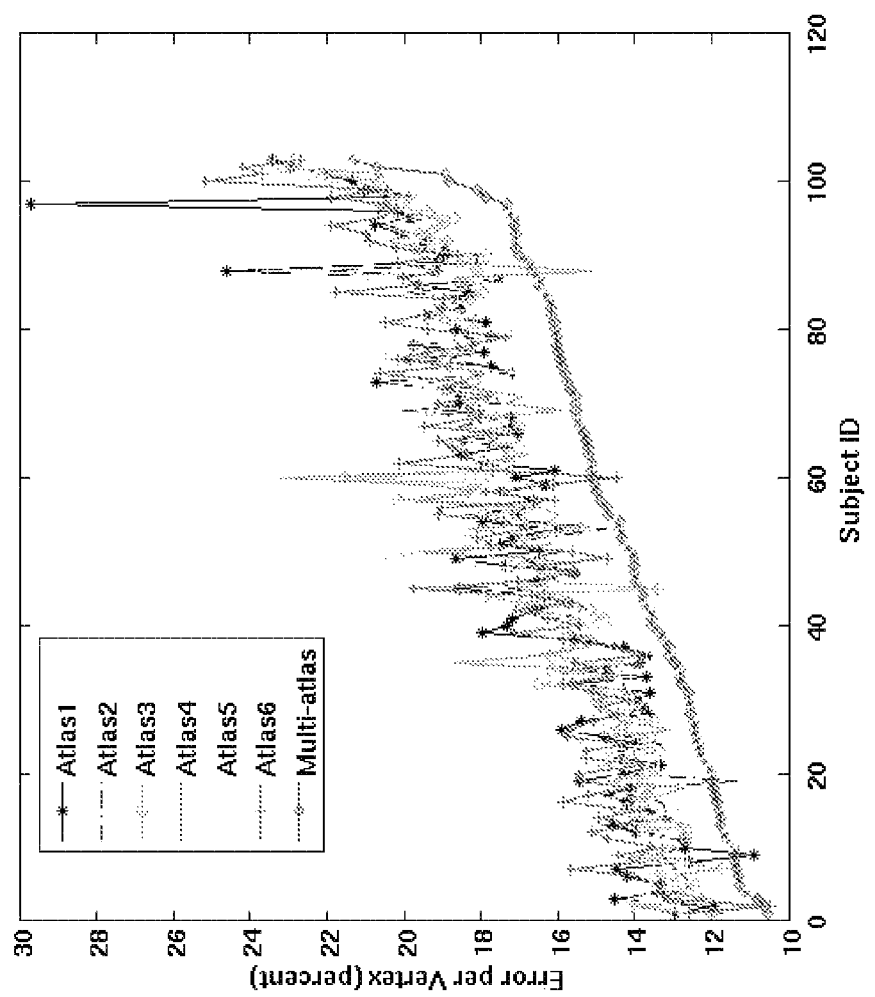

The preferred embodiment can proceed by the following steps, shown initially in FIG. 2 and FIG. 3:

Initially, a series of N, where N in one embodiment equaled 20, representative templates are formed, for test subjects having known degrees of AD. For each test subject, the PET and corresponding MRI images are obtained and aligned. Additionally, where CT scans are available, they can also be matched for the test subjects. From each PET and optional CT scan, a corresponding brain surface is computed.

The templates are stored in a database 21.

A new subject is then presented in the form of a PET scan and an optional CT scan where available 24.

The preferred embodiment then proceeds by the following steps:

Step 1: The new subject PET is aligned to the N templates, based on the PET scan and utilizing the optional CT scan where available.

Step 2: The N template brain surfaces are position relative to the subject PET. Each of the N template surfaces are treated as a surface mesh. For each point on the surface mesh, a comparison is made between the new subject PET value 26 and corresponding PET values 27, 28 at each of the templates, and a difference measure obtained.

Step 3: For each surface location, the M best template matches are stored based on the similarity between the new subject PET and the corresponding template PET.

Step 4. The M best template matches are used to derive M weights for each surface location. Using the template tissue maps, the M weights are utilized to fuse or weigh together the corresponding PET values to produce an overall PET value. The fusion occurs on a location by location basis.

Step 5: The results are displayed on an 'average brain surface', with the average brain surface being derived from a weighting of the template surfaces. With the PET values being displayed on the derived average brain surface 36. Because all the brain templates surfaces are co-registered together the candidate PET can be displayed on anyone of the template surface or on the average surface to represent the population.

Utilization of Optional CT Imagery

In a further optional refinement of the above embodiment, it is noted that present medical practice often facilitates the production of a CT type scan along with a PET scan in a combined PET/CT scanner. Where such scans are readily available, they are ideally utilized in the registration process. Whilst a CT scan does not provide for good tissue delineation, they do provide for very good fluid and bone delineation. Where a CT scan is available for a new subject, they can be utilized in a number of ways:

1. Initially, in step 1, the CT scan can be incorporated in aligning the corresponding PET scan with the templates. The CT scan will provide clear bone delineation of the new subject and can therefore be utilized in the alignment process.

Further, in step 4, given the CT of the patient is available, it is possible to estimate where the grey matter limit is as the CT will delineate the borders of the brain surface. The CT can therefore be utilized in correcting the grey matter calculation for the current PET scan, in border regions and thereby improve overall estimations.

Whilst the foregoing describes the operation of the preferred embodiment, a number of processing refinements and variations are available to the person skilled in the art when implementing the invention as discussed below:

1. Initial Image Preprocessing Template Creation: All captured PET imagery can initially subjected to preprocessing. This includes the intensity normalization of all the PiB PET images, and the preparation of brain templates. MRI scans are assumed only available for templates.

For the template dataset, it is necessary to pre-process the MRI image, the PET image and the surface of the interface between gray matter and white matter, or alternatively the surface between the gray matter and the CSF.

Firstly, each MRI image is spatially normalized to an atlas (in the example embodiment the atlas used was the Collins atlas: Collins, D., Zijdenbos, A., Kollokian, V., Sled, J., Kabani, N., Holmes, C., Evans, A., 1998. Design and construction of a realistic digital brain phantom. IEEE Trans. Med. Imag. 17 (3), 463-468.). Prior probability maps of the main tissues (GM, WM, and CSF) associated with the atlas were also utilized (in our case provided part of SPM with the atlas, Ashburner, J., Friston, K., 1999 "Nonlinear spatial normalization using basis functions" Hum. Brain Mapp. 7 (4), 254-26,). The atlas and associated prior can alternatively be computed easily from any database of images.

The MRI image and the PET image are co-registered by a locally rigid transform. The method used can be as disclosed in Ourselin, S., Roche, A., Subsol, G., Pennec, X., Ayache, N., 2001. Reconstructing a 3D structure from serial histological sections. Image Vis. Comput. 19 (1), 25-31.

After registration, the intensity values of the PET images are normalized by standard uptake value ratio (SUVR) (Lopresti B J, Klunk W E, Mathis C A, Hoge J A, Ziolko S K. Lu X, et al, "Simplified quantification of Pittsburgh compound B amyloid imaging PET studies: a comparative analysis", J Nucl Med 2005; 46:1959-72 Lopresti et al., 2005) was utilised to ensure inter and intra subject comparisons. SUVR is defined as the value of a region containing specific binding to one without specific binding. Cerebellar gray matter is often used as the referenced non-binding region as it is believed to be devoid of senile plaques (Joachim, C., Morris, J., Selkoe, D., 1989. Diffuse senile plaques occur commonly in the cerebellum in Alzheimer's disease. American J. Pathol. 135 (2), 309-319). The cerebellum mask from MRI is used to localize the region in PET image for the normalization. Finally, the interface surface between the gray matter and white matter is extracted from the segmented MRI images for each atlas.

This preprocessing step can be as set out in: Fripp J., Bourgeat P., Acosta O., Raniga P., Modat M., Pike E., Jones G., O'Keefe G., Masters L., Ames D., Ellis A., Maruff P., Currie J., Villemagne L., Rowe C., Salvado O., Ourselin S., 2008. Appearance modeling of 11C PiB PET images: characterizing amyloid deposition in Alzheimer's disease, mild cognitive impairment and healthy aging. Neuroimage 43 (3), 430-439.

The template preparation proceeds with a starting set of base images which can comprise a series of corresponding MRI and PET scan images for a collection of subjects.

A series of separate templates can be created. For each template, their MRI and PET images are co-registered (aligned) rigidly. The tissues are segmented on the template MRI images, and then the grey matter/white matter interfaces are determined. To allow users to inspect the interior cortical areas, the surfaces of the grey/white matter interfaces are separated into left and right hemispheres. Moreover, each template has a grey matter probability map created, which indicates how likely an image voxel belongs to grey matter.

The grey matter probability map can be created by standard intensity based segmentation methods using a Gaussian Mixture Model as described in the previous citation of Fripp et al.

2. Template Surface Registration: a multi-resolution EM-ICP method is applied to establish the correspondence among different template surfaces of grey/white matter interfaces. After surface registration, the template surfaces are re-sampled in order to share the same number of corresponding vertices. The EM-ICP method can be as set out in: Granger, S., & Pennec, X. (2002), "Multi-scale EM-ICP: A Fast and Robust Approach for Surface Registration", *Computer Vision—ECCV* 2002, 2353, 418-432 Springer, and Combes, B. and Prima, S., 2010 "An efficient EM-ICP algorithm for symmetric consistent non-linear registration of point sets" Medical Image Computing and Computer-Assisted Intervention (MICCAI), 594-601.

3. Registration for PET images: an affine/mild deformable registration between PET images of a specific subject and a corresponding template is performed to bring the surface and the probability map from the template space to the subject space.

The process of affine registration is illustrated by FIG. 3.

Alternatively, instead of using the transformed probability maps from templates, the probability map in the subject space can be generated by the nonlocal means segmentation on the subject PET image.

4. Surface-based Measurement by Multi-template Fusion: the mean grey matter PIB uptakes are measured along the normal directions of the transformed atlas surfaces separately guided by the corresponding transformed tissue probability map. Then the measurements are combined by a Bayesian network according to a local weighting scheme based on the local similarity between the transformed atlas PET image and the subject PET image. The similarity can be measured by normalized mutual information or other metrics.

Other Weighting Schemes can be Used.

For example, the M weights can be utilized in a weighted average in combining the corresponding template tissue indicators. Another alternative technique is that provided by a voting algorithm to determine a corresponding template tissue indicator.

As a further alternative, to fuse the results obtained from the selected multiple-templates, a Bayesian framework can be utilized as described below.

Given a PET image I(x), where x denotes an image voxel, the target is to measure the mean PiB uptake in gray matter along the normal directions of the transformed atlas surface $S^T$. That equals to estimate the expectation $E_{x \in \Delta}[\delta(I,x,l)]$, where $\delta(I,x,l)$ is an indicator function defines as follows:

$$\delta(I, x, l) = \begin{cases} I(x), & \text{for } l = 1 \\ 0, & \text{elsewhere} \end{cases}.$$

The symbol $\Delta$ denotes the intersection of the line along the normal direction of a surface vertex v and the PET image I. The symbol l is the tissue label, representing GM, WM and CSF with the values of 1, 2 and 3, respectively. The expectation can be calculated by $$E_{x \in \Delta}[\delta(I, x, l)] = \int_{x \in \Delta} \delta(I, x, l) p(I, x, l) dx \qquad (1)$$

$$= \int_{x \in \Delta} \delta(I, x, l) p(l | I, x) p(I, x) dx$$

$$= \int_{x \in \Delta} I(x) p(l = 1 | I, x) p(I, x) dx.$$

Taking discrete probability, results in the following:

$$E_{x \in \Delta}[\delta(I,x,l)] = \Sigma_{x \in \Delta} I(x) P(l=1|I,x) P(I,x). \qquad (2)$$

Assuming that x is evenly sampled from $\Delta$, the probability $$P(I, x) = \frac{1}{|\Delta|},$$

where $|\Delta|$ is the length of $\Delta$. The posterior label probability P(l|I,x) is estimated from the transformed templates $A_i^T$(i=1 ... n, where n is the number of templates selected) by maginalizing the joint probability $P(l, A_i^T|I,x)$:

$$P(l|I,x) = \Sigma_{i=1}^n P(l, A_i^T|I,x) = \Sigma_{i=1}^n P(l|A_i^T,I,x) P(A_i^T|I,x). \qquad (3)$$

Here $P(l|A_i^T,I,x)$ represents the probability for the voxel x to be GM in the transformed template $A_i^T$, which can be obtained from the transformed template probability maps.

The probability $P(A_i^T|I,x)$ measures the probability of the voxel x to be well aligned between the test image I and the transformed template $A_i^T$. In our approach, $P(A_i^T|I,x)$ is set proportional to the reciprocal of the metric of normalized mutual information estimated locally within the neighbourhood N(x) of x. That is, $P(A_i^T|I,x)=P(A_i^T|I,N(x))$. Due to the low resolution of PET images, the size of N(x) should not be too small, otherwise the resulting mutual information will fit the noise. In measurements conducted, N(x) was set to be 30×30×30, which covers all the voxels along the line $\Delta$. Therefore, $P(A_i^T|I,N(x))$ was constant with respect to the variable x(x$\in\Delta$).

Combining (2) and (3), results in:

$$E_{x \in \Delta}[\delta(I, x, l)] = \frac{1}{|\Delta|} \sum_{x \in \Delta} I(x) P(l = 1 | I, x) \qquad (4)$$

$$= \frac{1}{|\Delta|} \sum_{x \in \Delta} \left( I(x) \sum_{i=1}^n P(l = 1 | A_i^T, I, x) P(A_i^T | I, x) \right)$$

$$= \sum_{i=1}^n P(A_i^T | I, N(x)) \left( \frac{1}{|\Delta|} \sum_{x \in \Delta} I(x) P(l = 1 | A_i^T, I, x) \right)$$

Equation (4) shows the additive property for the estimation of the mean PiB retention at each surface vertex: the estimation from multiple atlases can be attained by independent estimation from each single atlas and then linearly combined in a weighted way. The combination weights $P(A_i^T|I,N(x))$ reflect the alignment between the test image I and the transformed templates $A_i^T$. As the alignment is assessed by local metric, such a combination is nonlinear for the whole surface. This additive property is favourable for the approach when the template set needs to be dynamically determined. It makes the switch of selected templates easy by confining the changes to the affected templates only.

When conducting individual estimation from a single template $A_i^T$, the PiB value I(x) is weighted by its probability as a gray matter voxel, that is, $P(l=1|A_i^T,I,x)$. This implicitly defines a gray matter region with a soft boundary, which reflects the variation observed in the training population. Therefore, the proposed estimation may improve the robustness to the registration error than a hard gray matter segmentation as disclosed in the prior art.

Using multiple templates was found to improve the estimations from individual templates. An example of the improvements obtained in testing is illustrated in FIG. 5 to FIG. 8.

5. Surface Visualization: once the surface based measurements have been performed, for each subject, the left and right hemispheres are put together and visualized from eight perspectives. Screen-shots can be automatically taken, which may be useful for visual inspection or generating further reports.

Figures 9, 10:
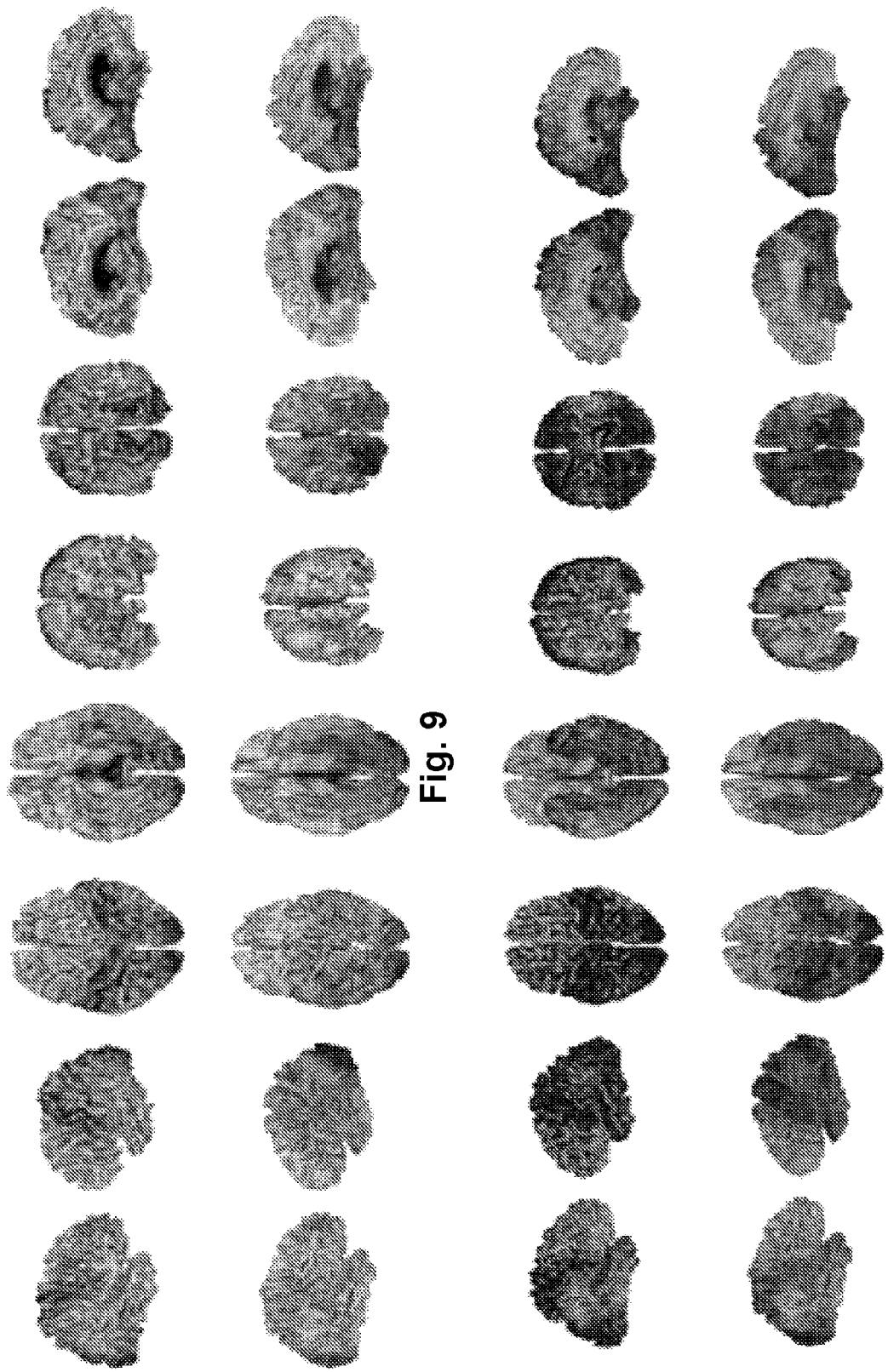
FIG. 9 illustrates an example mapping for an AD patient.
FIG. 10 illustrates an example mapping for a normal patient.

Example results of one AD and one normal control are given in FIG. 9 and FIG. 10 respectively.

Interpretation

The following description and figures make use of reference numerals to assist the addressee understand the structure and function of the embodiments. Like reference numerals are used in different embodiments to designate features having the same or similar function and/or structure.

The drawings need to be viewed as a whole and together with the associated text in this specification. In particular, some of the drawings selectively omit including all features in all instances to provide greater clarity about the specific features being described. While this is done to assist the reader, it should not be taken that those features are not disclosed or are not required for the operation of the relevant embodiment.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of exemplary embodiments of the invention, various features of the invention are sometimes grouped together in a single embodiment, Fig., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

We claim:

1. A method of determining the degree of uptake of a PET marker in an individual candidate PET scan, the method including the steps of:
   (a) calculating a series of representative matched controlled PET and MRI templates for a series of controlled sample scans of individuals;
   (b) computing a series of brain surfaces from the matched templates;
   (c) aligning the individual candidate PET scan with the matched templates;
   (d) aligning the series of brain surfaces with the candidate PET scan, wherein each of the brain surfaces aligned with the candidate PET scan includes a plurality of surface locations;
   (e) selecting M templates for each of the plurality of surface locations based on a similarity measure between the candidate PET scan and a corresponding controlled PET template;
   (f) computing M weights for each of the plurality of surface locations utilizing a corresponding MRI template tissue map;
   (g) utilizing the M weights to combine the M templates for each of the plurality of surface locations to form an average brain surface indicator.

2. A method as claimed in claim 1 further comprising the step of:
   (h) combining the average brain surface indicator with the candidate PET scan to create an averaged brain surface for display.

3. A method as claimed in claim 1 wherein step (c) further comprises utilizing candidate CT or X-Ray scan data in the alignment of the candidate PET scan with the series of matched templates.

4. A method as claimed in claim 1 wherein the matched templates and candidate PET scan are segmented.

5. A method as claimed in claim 1 wherein said step (g) includes utilising the M weights as a weighted average in combining the M templates.

6. A method as claimed in claim 1 wherein said step (g) includes utilising the M weights in a voting algorithm to determine a corresponding template tissue indicator.

7. An apparatus configured to implement the method of claim 1.

8. A method of determining the degree of uptake of an imaging marker in an individual candidate imaging marker scan, the method including the steps of:
   (a) calculating a series of representative matched controlled imaging marker scan templates and tissue marker templates for a series of controlled sample scans of individuals;

(b) computing a series of internal body delineation surfaces from the matched templates;
(c) aligning the individual candidate imaging marker scan with the matched templates;
(d) aligning the individual candidate imaging marker scan with the series of body delineation surfaces, wherein each of the body delineation surfaces aligned with the individual candidate imaging marker scan includes a plurality of surface locations;
(e) selecting M templates for each of the plurality of surface locations based on a similarity measure between the candidate imaging marker scan and a corresponding controlled imaging marker scan template;
(f) computing M weights for each of the plurality of surface locations utilizing a corresponding tissue marker template;
(g) utilizing the M weights to combine the M templates for each of the plurality of surface locations to form an average brain surface indicator.

9. A method as claimed in claim 8 wherein the imaging marker scan templates comprise Positron Emission Tomography (PET) scan templates or Single-photon emission computed tomography (SPECT) scan templates.

10. A method as claimed in claim 8 wherein each tissue marker template is calculated from images of different subjects with known image properties.

11. A method as claimed in claim 10 wherein the tissue marker templates are selected from a wider set of templates in accordance with similar characteristics of a candidate, from which the individual candidate imaging marker scan is obtained, and subjects with known image properties.

\* \* \* \* \*